(12) United States Patent
Hu et al.

(10) Patent No.: US 9,734,430 B2
(45) Date of Patent: Aug. 15, 2017

(54) EVALUATION SYSTEM OR DETERMINATION OF CARDIOVASCULAR FUNCTION PARAMETERS

(71) Applicants: Mackay Memorial Hospital, Taipei (TW); CHung Yuan Christian University, Taoyuan (TW)

(72) Inventors: Wei-Chih Hu, Taoyuan (TW); Chung-Lieh Hung, Taipei (TW); Hung-I Yeh, Taipei (TW)

(73) Assignees: MacKay Memorial Hospital, Taipei (TW); Chung Yuan Christian University, Taoyuan (TW)

( * ) Notice: Subject to any disclaimer, the term of this patent is extended or adjusted under 35 U.S.C. 154(b) by 14 days.

(21) Appl. No.: 14/854,812

(22) Filed: Sep. 15, 2015

(65) Prior Publication Data

US 2016/0004933 A1 Jan. 7, 2016

Related U.S. Application Data

(63) Continuation-in-part of application No. 13/568,982, filed on Aug. 7, 2012, now abandoned.

(30) Foreign Application Priority Data

Jan. 2, 2012 (TW) .............................. 101100106 A

(51) Int. Cl.
*G06K 9/00* (2006.01)
*G06K 9/62* (2006.01)
(Continued)

(52) U.S. Cl.
CPC ............ *G06K 9/6207* (2013.01); *A61B 5/029* (2013.01); *A61B 5/0263* (2013.01); *A61B 6/032* (2013.01);
(Continued)

(58) Field of Classification Search
None
See application file for complete search history.

(56) References Cited

U.S. PATENT DOCUMENTS 6,106,466 A * 8/2000 Sheehan .............. A61B 5/1075
128/916
6,346,124 B1 2/2002 Geiser et al.
(Continued)

*Primary Examiner* — Weiwen Yang
(74) *Attorney, Agent, or Firm* — Juan Carlos A. Marquez; Marquez IP Law Office, PLLC

(57) ABSTRACT

An evaluation system for determination of cardiovascular function parameters is provided. The evaluation system includes a data reading module, an image generating module, a contour determination module, an active contour module, a geometric center axis computing module, a view angle selection module and a function evaluation module. After reading cardiovascular graphic files with the data reading module, the image generating module displays 2D images or a 3D image constructed from the 2D images. Then, active contours are generated by the contour determination module and the active contour module, so as for the geometric center axis computing module to calculate geometric center axes. The view angle selection module then rotates the 3D image according to the view angle data received and modifies the 2D image files accordingly to generate plural cross-section images of the 3D image. Finally, the function evaluation module calculates evaluation parameters according to the geometric center axes. Thus, evaluation parameters can be derived from cardiovascular ultrasound images for clinical diagnosis in the evaluation of cardiovascular functions.

11 Claims, 25 Drawing Sheets

(51) Int. Cl.
*G06T 7/00* (2017.01)
*G06T 7/60* (2017.01)
*A61B 6/03* (2006.01)
*A61B 6/00* (2006.01)
*A61B 5/026* (2006.01)
*A61B 5/029* (2006.01)
*A61B 8/06* (2006.01)

(52) U.S. Cl.
CPC .............. *A61B 6/503* (2013.01); *A61B 8/065* (2013.01); *G06T 7/0012* (2013.01); *G06T 7/0083* (2013.01); *G06T 7/606* (2013.01); *G06T 2207/10016* (2013.01); *G06T 2207/10132* (2013.01); *G06T 2207/30048* (2013.01)

(56) References Cited

U.S. PATENT DOCUMENTS

| | | |
|---|---|---|
| 6,716,175 B2 * | 4/2004 | Geiser ................... G06T 7/0012 600/450 |
| 6,757,414 B1 | 6/2004 | Turek et al. |
| 7,421,101 B2 * | 9/2008 | Georgescu ................ G06T 7/20 382/103 |
| 7,603,154 B2 | 10/2009 | Noble et al. |
| 2011/0243401 A1 | 10/2011 | Zabair et al. |

* cited by examiner

EVALUATION SYSTEM OR DETERMINATION OF CARDIOVASCULAR FUNCTION PARAMETERS

CROSS-REFERENCE TO RELATED APPLICATIONS

The present application is a continuation-in-part of U.S. application Ser. No. 13/568,982 filed on Aug. 7, 2012, titled "EVALUATION SYSTEM FOR DETERMINATION OF CARDIOVASCULAR FUNCTION PARAMETERS USING ULTRASOUND IMAGES", which claims priority to Taiwan Application No. 101100106 filed Jan. 2, 2012, the disclosures of which are hereby incorporated by reference herein.

BACKGROUND OF THE INVENTION

1. Technical Field

The present invention relates to an evaluation system for determination of cardiovascular function parameters and, more particularly, to such an evaluation system for use in clinical diagnosis.

2. Description of Related Art

Cardiac function parameters such as the ejection fraction and the ventricular volume are typically evaluated by nuclear medicine diagnosis, and this has been the case for quite a long time. Basically, the evaluation process involves injecting a radioactive tracer (e.g., TC-99m) into a patient's or a test subject's body, allowing the tracer to be distributed evenly in the patient's or the test subject's blood. Then, by detecting the distribution, and variation thereof, of the radioactive tracer in the patient's or the test subject's heart with a nuclear medicine imaging apparatus, the ejection fraction and the ventricular volume can be evaluated. As radioactive tracers are harmful to the human body, it is highly desirable that cardiac function parameters can be directly derived from images obtained by non-invasive photographic techniques that feature non-ionizing radiation, with a view to reducing patients' and test subjects' exposure to radiation.

U.S. Pat. No. 7,603,154 discloses a method for estimating the left ventricular (LV) volume during a cardiac cycle using endocardial contours in three-dimensional (3D) cardiac images taken at end diastole, wherein the contours can be manually specified or semi-automatically derived. Based on the contours and on the pixel intensity of all the images, the LV volume is estimated according to intensity variations within the area enclosed by the contours. The ventricular volume and the ejection fraction can be derived in this way because the intensity variations are related to the change in size of the ventricle.

While U.S. Pat. No. 7,603,154 discloses a method whereby function parameters related to the ventricular volume can be derived from 3D cardiac images, the calculation of other cardiac function parameters (e.g., a ventricular wall displacement parameter) remains unsolved. Nowadays, methods for obtaining cardiovascular images by non-ionizing radiation techniques and deriving cardiac function parameters other than those related to the ventricular volume from the cardiovascular images in real time are still unavailable. Hence, there is a need to develop a method by which cardiovascular function parameters other than those related to the ventricular volume can be evaluated using cardiovascular ultrasound images.

BRIEF SUMMARY OF THE INVENTION

The present invention discloses an evaluation system for determination of cardiovascular function parameters, wherein the evaluation system includes a data reading module, an image generating module, a contour determination module, an active contour module, a geometric center axis computing module, an image generating module and a function evaluation module. The present invention aims to achieve real-time evaluation of cardiovascular functions by means of ultrasound images.

The present invention provides an evaluation system implemented in a computer hardware system and configured for determination of cardiovascular function parameters. The evaluation system includes: a data reading module for reading at least one graphic file, each graphic file including a plurality of 2D image files that are related to one another and are successively created at a plurality of time points in a time sequence; an image generating module for displaying the 2D image files as a plurality of 2D images or a 3D image constructed from the 2D images; a contour determination module for receiving point selection information generated by a user by selecting points in any said 2D image corresponding to an initial said time point, and for determining an initial contour in each said 2D image corresponding to the initial time point according to the point selection information; an active contour module for reading the initial contours and determining the active contour in each 2D image; a geometric center axis computing module for reading the active contours and computing the geometric center axis corresponding to each time point; a view angle selection module, which receives a view angle data, rotates the 3D image according to the view angle data and modify the 2D image files read by the data reading module accordingly to generate plural cross-section images of the 3D image relative to the view angle data received; and a function evaluation module for successively computing the difference between the active contours corresponding to each time point in the time sequence and the corresponding geometric center axis, so as to generate an evaluation parameter.

Implementation of the present invention at least involves the following inventive steps:

1. 3D cardiovascular images can be shown in real time to enable calculation of cardiovascular evaluation parameters.
2. Abnormal myocardial wall activity as well as the volume and distribution of the pericardium can be detected in real time both qualitatively and quantitatively in 360 degrees.
3. Cross-section images of any selected view angle can be constructed for ease of diagnosis.
4. Real time 3D image together with real time 2D images can be obtained.
5. Analysis across adjacent and yet different cardiac structures can be made.
6. Simultaneous multiple-organ dynamic data acquisition and image analysis of cardiac ventricular, atriums and pulmonary can be made.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

Figure 1A:
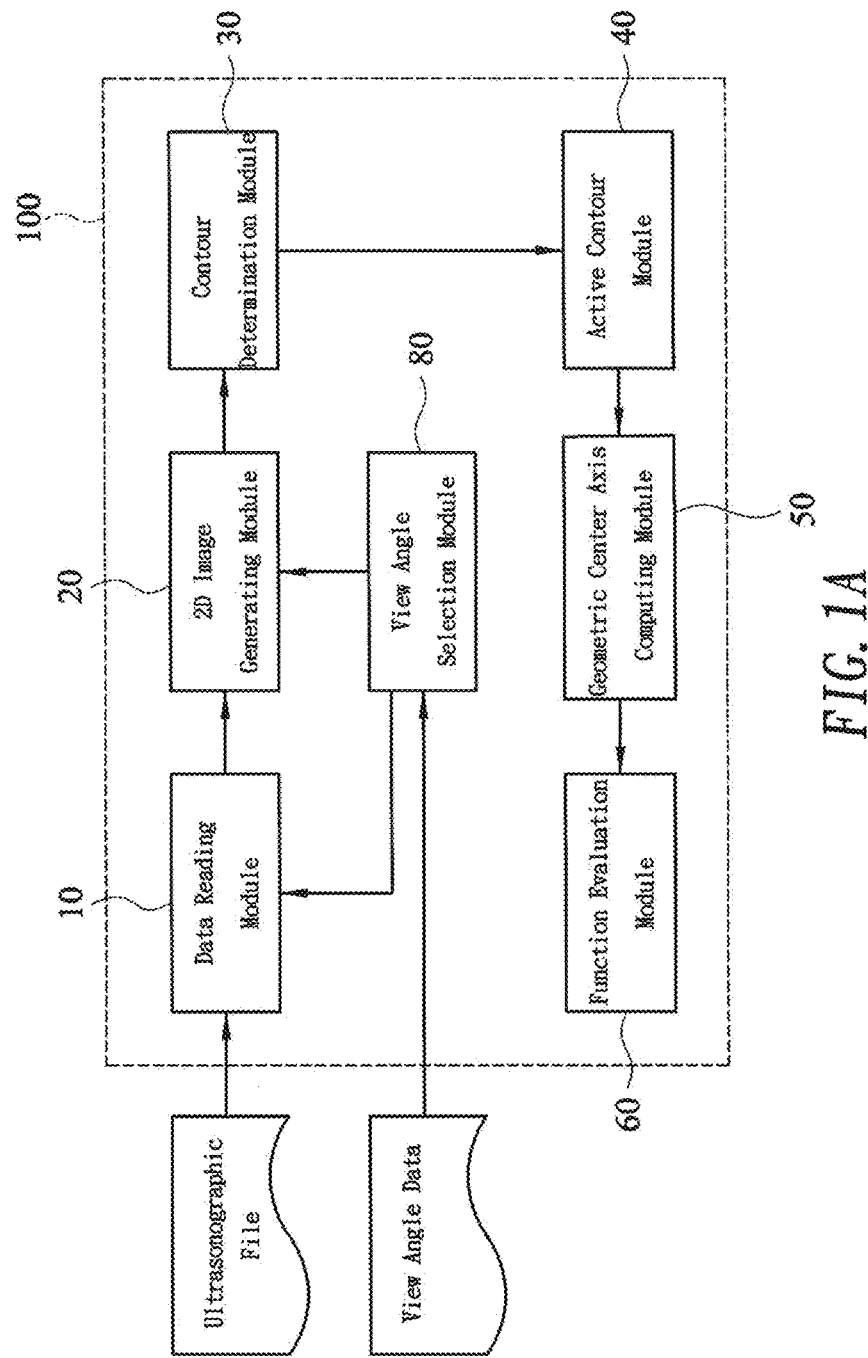
FIG. 1A is a block diagram showing the first aspect of an evaluation system according to an embodiment of the present invention.

As shown in FIG. 1A, is an embodiment of an evaluation system 100 for determination of cardiovascular function parameters that is implemented in a computer hardware system that includes at least an input/output unit, a memory unit, a logic operation unit and a control unit. The evaluation system 100 itself includes a data reading module 10, an image generating module 20, a contour determination module 30, an active contour module 40, a geometric center axis computing module 50, a view angle selection module 80 and a function evaluation module 60.

The data reading module 10 is configured for reading at least one graphic file created by scanning a clinical patient's or a test subject's cardiovascular structures with an ultrasonographic apparatus. Each graphic file includes a plurality of related 2D image files of different cross-sections, taken from top down, of the cardiovascular structures. More particularly, each cross-section has a series of 2D image files created successively at a plurality of time points (or time frames) in a time sequence.

Each graphic file can be a Digital Imaging and Communications in Medicine (DICOM) file recorded in the DICOM file format, which essentially includes a header and a data set, or a CT (computer tomography) data file, a MRI data file or an ultrasonographic data file. When reading such a graphic file, the data reading module 10 identifies the information in the header, i.e., the patient's basic data and the attributes of the imaging module (e.g., the image capturing speed and the width and height of each image). The information is identified for subsequent processing and use.

The image generating module 20 is configured for constructing information of the data set using the 2D image files read by the data reading module 10 and the imaging module attributes read from the header, so that the 2D image files can be displayed as a plurality of 2D images or a 3D image constructed from the 2D images. However, the displaying of the 2D images or the 3D image may be inconsistent for the following reasons. First of all, as the length of the aforesaid time sequence varies with people's heart rates, the number of time points (or frames) in the time sequence corresponding to a certain heart rate will be different from that corresponding to another. Moreover, the fact that each person's cardiovascular structures vary in size leads to different numbers of cross-sections. In consideration of this, the image sequence in the present embodiment is established according to the queuing order in the data structure, as explained below. To begin with, the head pointer is pointed to the first 2D image, and the tail pointer to the last 2D image. Then, a transient pointer is used to find the 2D image of each cross-section. By doing so, the image generating module 20 can generate real time 2D images and a real time 3D image constructed from the real time 2D images without limitations in the number of cross-sections or in the length of the time sequence.

Figure 2:
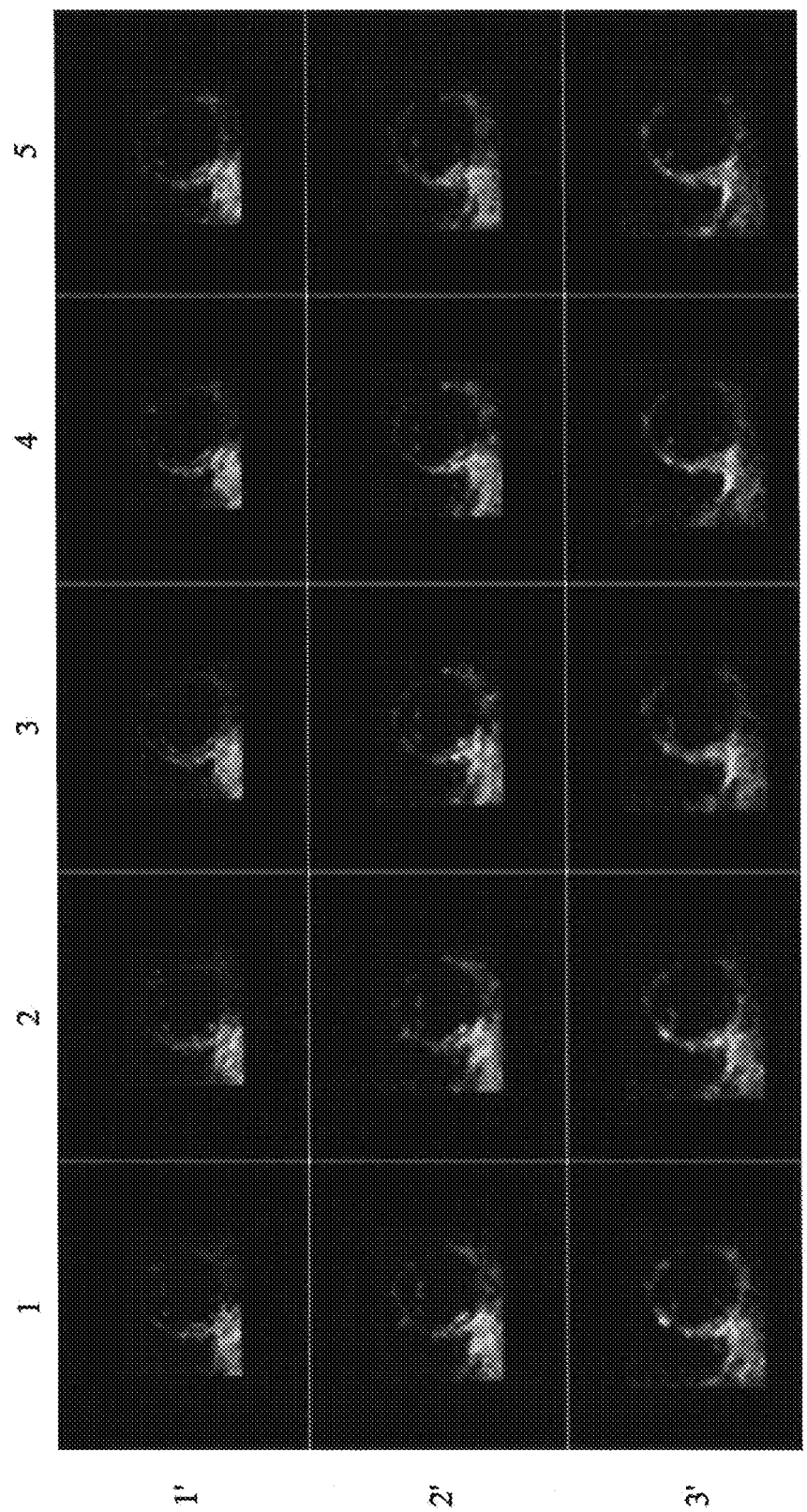
FIG. 2 is an image sequence diagram showing the data structure according to an embodiment of the present invention.

Afterward, referring to FIG. 2, the image generating module image generating module 20 displays on a computer screen the 2D images corresponding to all the time points (or frames) and all the cross-sections, in a way similar to a video wall. For instance, the image generating module 20 displays the cross-sections 1~n corresponding to the frame 1', the cross-sections 1~n corresponding to the frame 2', and so on. By means of a cursor and a scroll wheel, a user not only can easily view the images corresponding to all the frames in a time sequence, but also can choose between the processed images and the original (i.e., unprocessed) images.

Figure 3A:
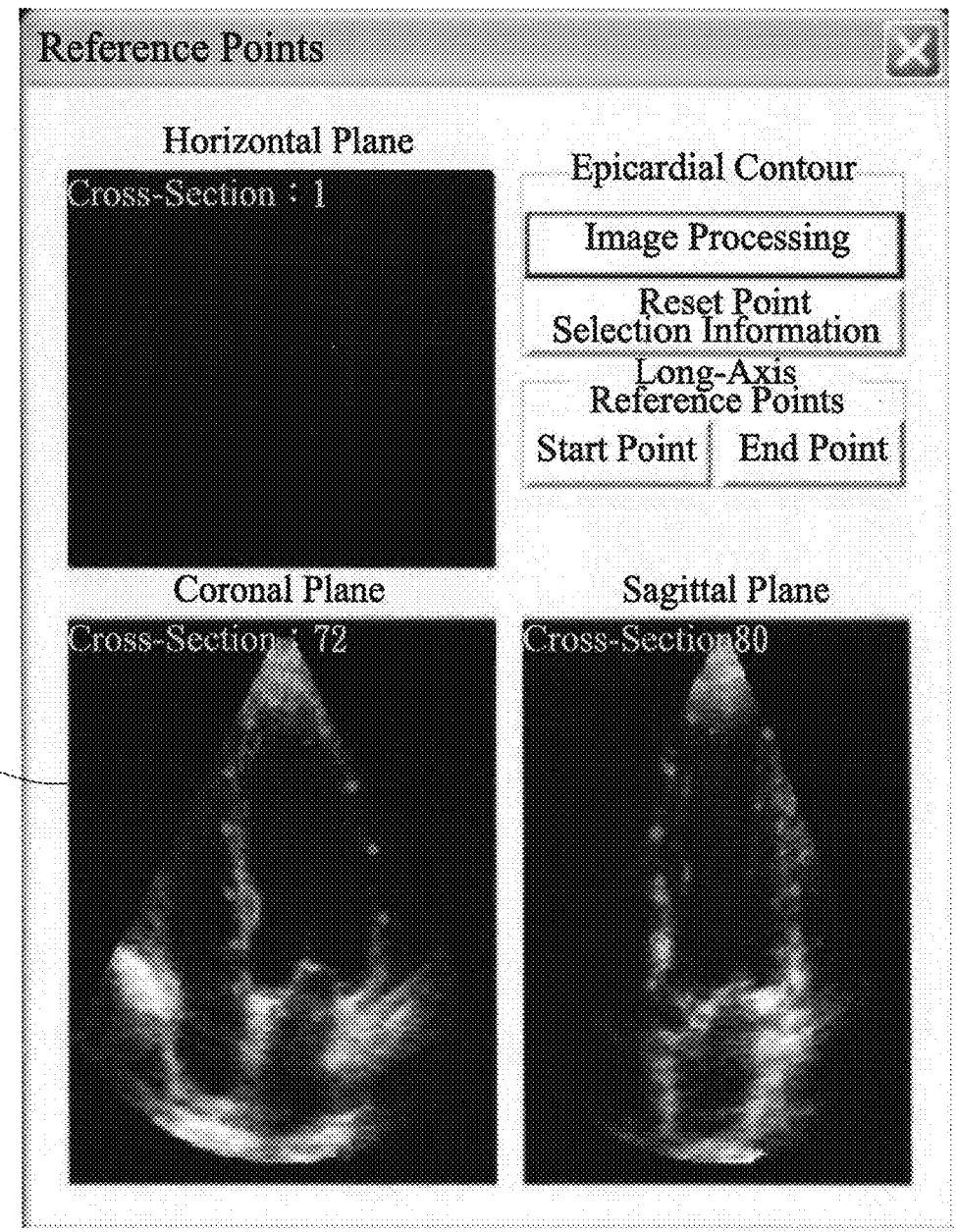
FIG. 3A schematically shows the reference points for an epicardial contour according to an embodiment of the present invention.

Referring to FIG. 3A, the contour determination module 30 is configured for receiving point selection information generated by a user by selecting points in any of the 2D images on the screen, thus saving the time otherwise required for manual contouring. The point selection information can be a plurality of reference points. Based on the general information provided by the point selection information, the contour determination module 30 performs computation and thereby determines the initial contour in each of the 2D images corresponding to the initial time point according to the point selection information. The initial contour may include an initial endocardial contour and an initial epicardial contour. It should be noted that the point selection information can only be generated from those 2D images that correspond to the initial time point (or frame). Hence, the initial contours are determined only for those 2D images that correspond to the initial time point (or frame).

For example, the contour determination module 30 receives a plurality of epicardial contour reference points 31 which are manually selected by the user from the 2D images in the coronal plane and in the sagittal plane. These epicardial contour reference points 31 are selected at intervals along the epicardial contours in the 2D images according to the user's judgment and experience and will be used to generate closed curves that delineate the epicardial contours.

Figure 3B:
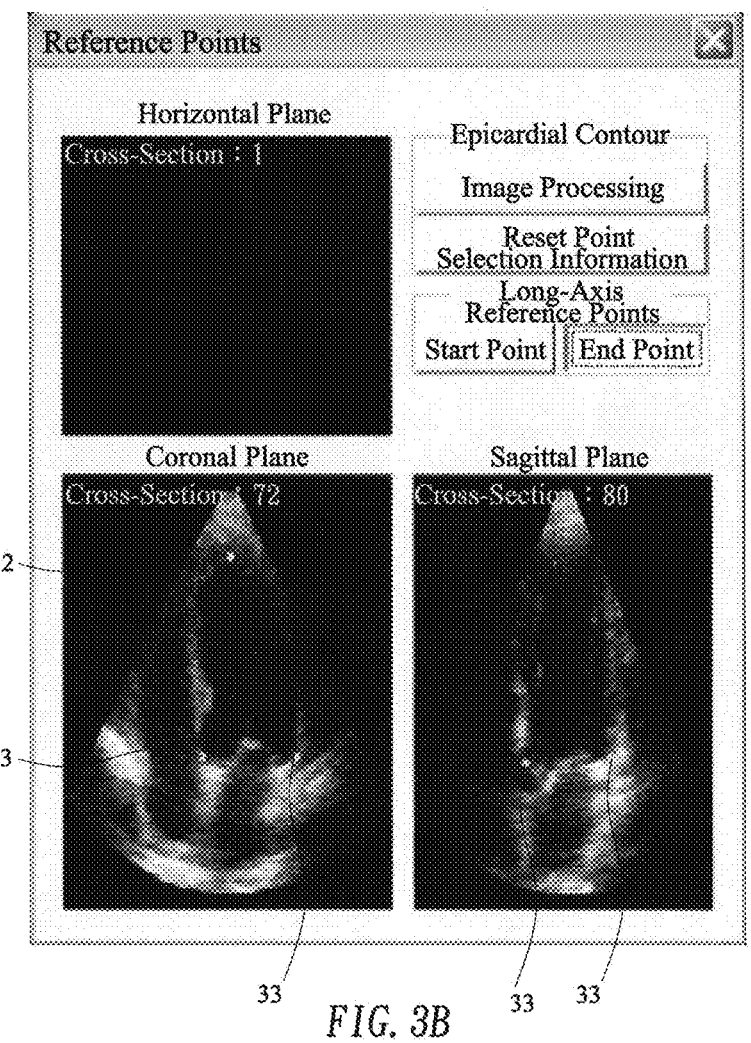
FIG. 3B schematically shows the reference points for the positions of the apex and the base of the heart according to an embodiment of the present invention.

Then, referring to FIG. 3B, the heart apex position reference point 32, which serves as the starting cross-section in the processing process, is set using the Start Point button under Long-Axis Reference Points, and the End Point button is used to set two heart base position reference points 33 in each of the coronal-plane and sagittal-plane 2D images, thereby defining the terminal cross-section in the processing process. Since the coronal plane and the sagittal plane are perpendicular to each other, the four heart base position reference points 33 jointly define the terminal cross-section. If the point selection information needs resetting, the Reset Point Selection Information button can be used to start re-selection of the points.

Figure 3C:
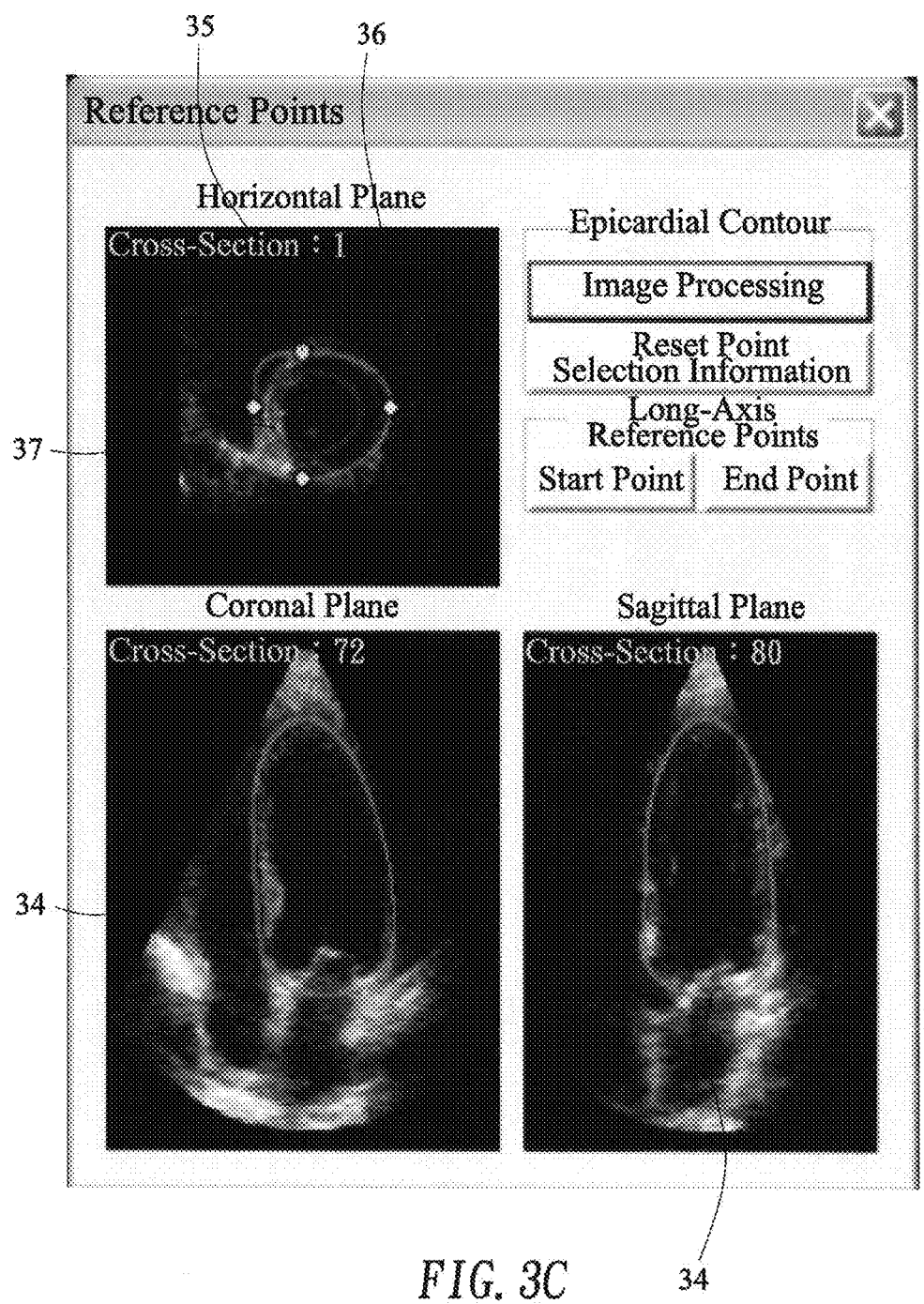
FIG. 3C schematically shows an initial contour according to an embodiment of the present invention.

Referring to FIG. 3C, once the Image Processing button is pressed, the contour determination module 30 uses a B-spline interpolation function to interpolate the manually selected epicardial contour reference points 31 and thereby generates closed curves 34. The more accurate the epicardial contour reference points 31 are, the more the closed curves 34 will conform to the epicardial contours in the 2D images. By projecting the two closed curves 34, which are generated from the point selection information and lie in the coronal plane and the sagittal plane respectively, to each position-related cardiac 2D image in the horizontal plane, four projected reference points 35 are obtained. Then, an initial contour is determined as follows. An initial epicardial contour 36 is determined by applying a cubic spline function to the projected reference points 35, and an initial endocardial contour 37 is determined by applying a B-spline interpolation function to the projected reference points 35.

Figure 4A:
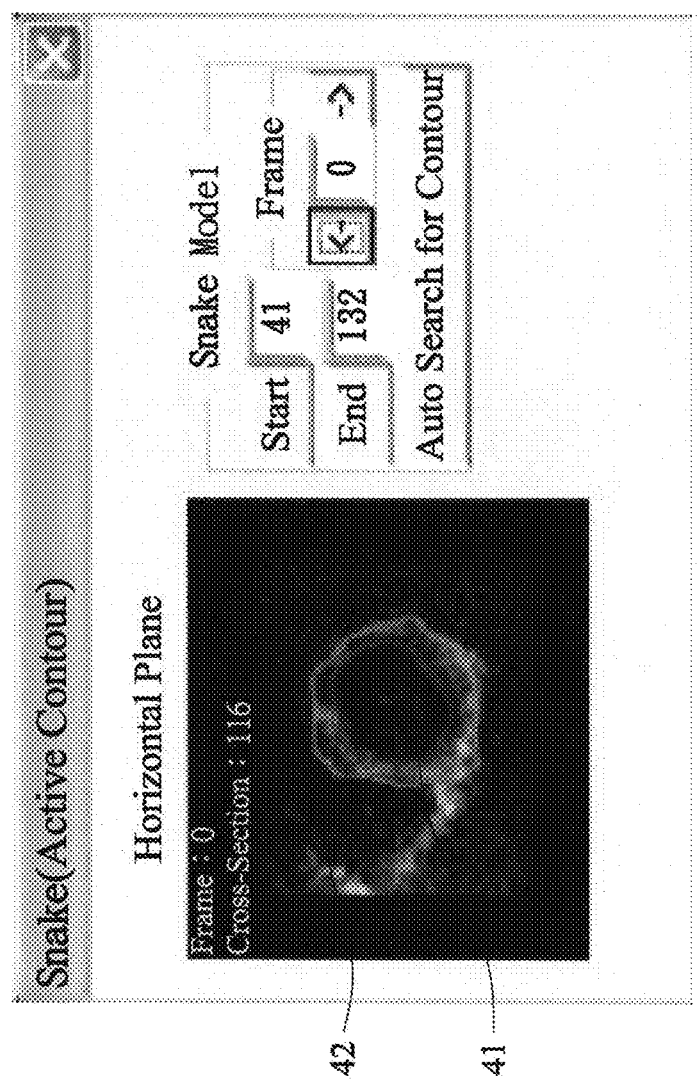
FIG. 4A schematically shows an active contour module interface according to an embodiment of the present invention.
Figure 4B:
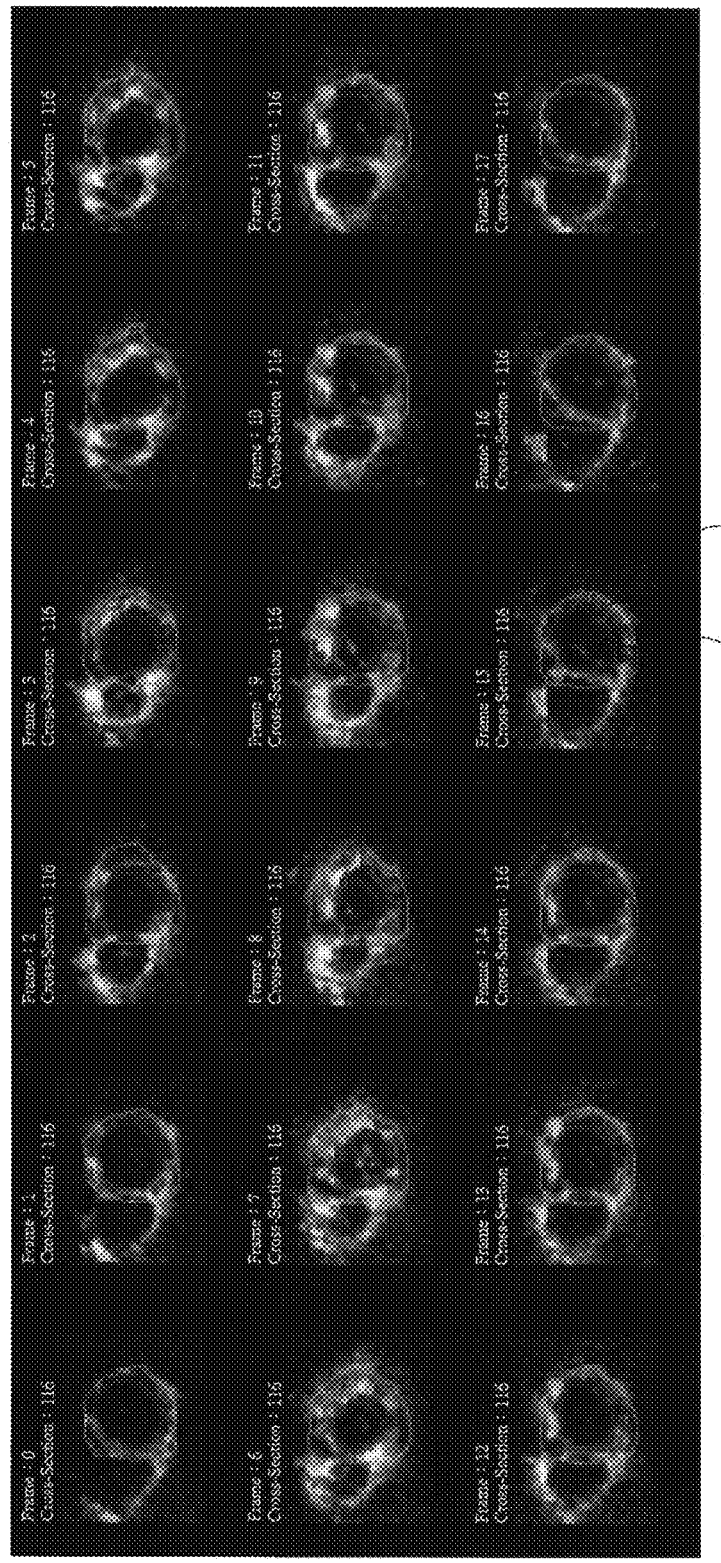
FIG. 4B is an image sequence diagram showing active contours according to an embodiment of the present invention.

The function of the active contour module 40 is described below with reference to FIGS. 4A and 4B. To begin with, the active contour module 40 reads the initial contours generated by the contour determination module 30 for all the cross-sections corresponding to the initial time point (or frame). Then, by pressing the Auto Search for Contour button, the active contour module 40 is triggered to compute with the Snake model so that the initial contour corresponding to the 2D image on display approaches the real contour in the image. The resultant new contour is used as the starting contour for the following frame, and the computation can be repeated until an active contour is created for each 2D image of the same cross-section. Thus, the active contour in each cross-section at each user-selected frame is obtained. Each active contour may include an active endocardial contour 41 and an active epicardial contour 42, wherein the active endocardial contour 41 is created based on the corresponding initial endocardial contour 37, and the active epicardial contour 42 is created based on the corresponding initial epicardial contour 36. When the images with the active contours are displayed in a manner similar to a video wall, as shown in FIG. 4B, variations of the endocardial contours 41 and of the epicardial contours 42 from diastole to systole can be clearly observed.

The geometric center axis computing module 50 is configured for computing the geometric center axis of the heart, which features an irregular shape and continuous contraction and relaxation. More particularly, the geometric center axis computing module 50 reads the active contours generated by the active contour module 40 (which active contours include the active contour in each cross-section at each time frame), computes the center of each active contour, and generates a geometric center axis by connecting the computed centers of the active contours in all the cross-sections at the same time point (or frame).

Figure 5:
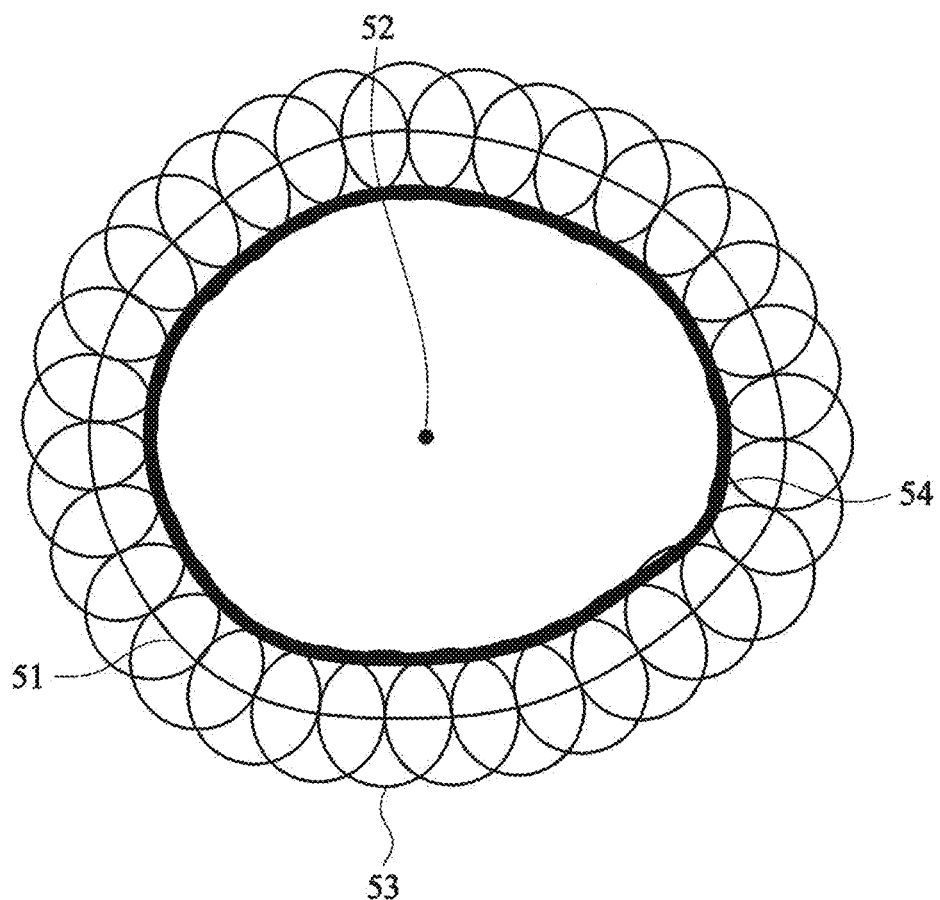
FIG. 5 schematically shows a curvature method according to an embodiment of the present invention.

Referring to FIG. 5, the center 52 of the active contour 51 is determined by a curvature method as follows. To start with, the center of a small circle 53 is moved along the active contour 51 such that each two adjacent traces of the circle 53 intersect each other both inside and outside the active contour 51 and thereby define an inner intersection point and an outer intersection point respectively. The inner intersection points jointly form a new closed curve 54. By moving the center of another small circle along the new closed curve 54, a smaller closed curved is formed. The foregoing steps are repeated until the center 52 is obtained in a converging manner.

Thus, each time point (or frame) in the time sequence has a geometric center axis, and the plural geometric center axes in the time sequence change and move with the relaxing and contracting cycle of the heart. These geometric center axes are collectively referred to as the mechanical center axis of the heart. It has been observed that the mechanical center axis of the heart is relatively close to the aorta during systole and to the mitral valve during diastole. As the ventricular wall moves simultaneously with the mechanical center axis of the heart, the actual contraction and relaxation conditions of the heart cannot be accurately evaluated without knowing the variation in the distance between the ventricular wall and the geometric center axis of the heart.

Figure 1B:
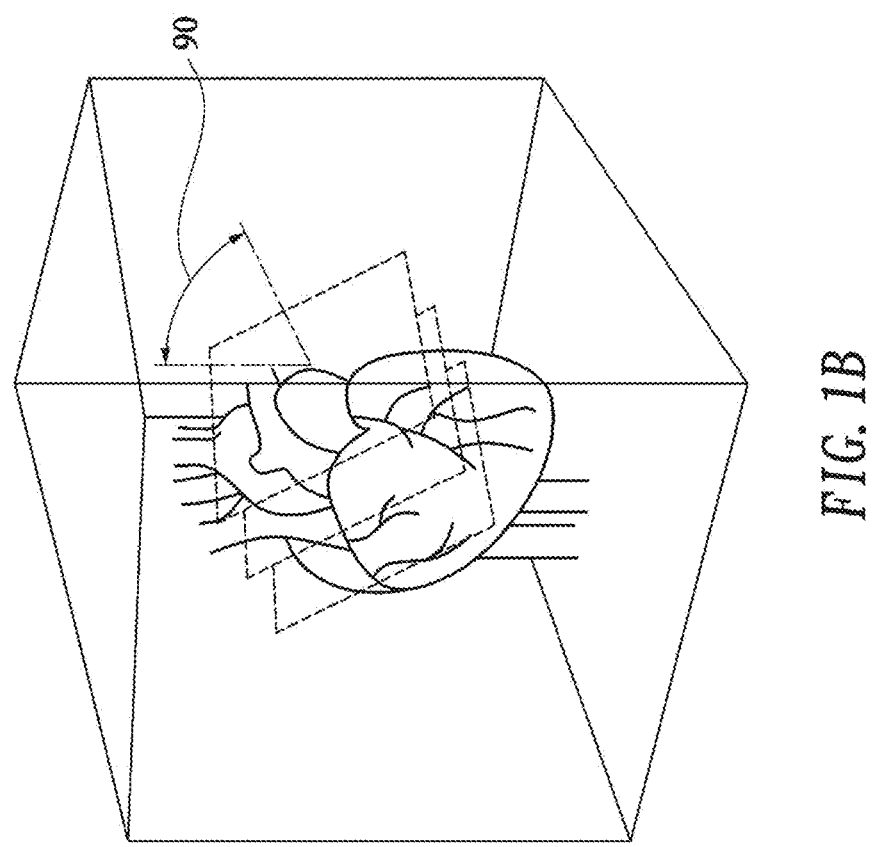
FIG. 1B is a perspective view of slices of cross-section of a view angle according to an embodiment of the present invention.

Please refer to FIG. 1A and FIG. 1B, a view angle selection module 80 which receives a view angle data 90, rotates the 3D image according to the view angle data 90 and modify the 2D image files read by the data reading module 10 and accordingly to generate plural cross-section images of the 3D image relative to the view angle data 90.

The above mentioned view angle data 90 can be an input data from a man-machine-interface or a user interface (UI) connected to the view angle selection module 80 of the evaluation system 100. Examples of man-machine-interface or user interface (UI) are at least a mouse, a keypad, a key board or a touch panel. Further, the view angle data 90 can also be a received data or data file output from a PC, a portable device or another medical instrument.

Thus, cross-section images of whatever view angle data 90 required of the 3D image can be generated by the evaluation system 100 with the application of the view angle selection module 80 for ease of diagnosis of cardiac function, heart function or lung status.

The thickness of the object under observation represented by each of the cross-section image can be set to about 0.5 mm for ease of observation into small details obtained from the object under observation.

Referring back to FIG. 1A, the function evaluation module 60 successively computes the difference between each active contour and the corresponding geometric center axis (i.e., the distance between each active contour and its center) at each time point in the time sequence and generates a cardiac function evaluation parameter based on the differences thus obtained, among other information. The evaluation parameter can be a volume parameter, a displacement parameter, a deformation parameter, or a speed parameter.

Figure 6:
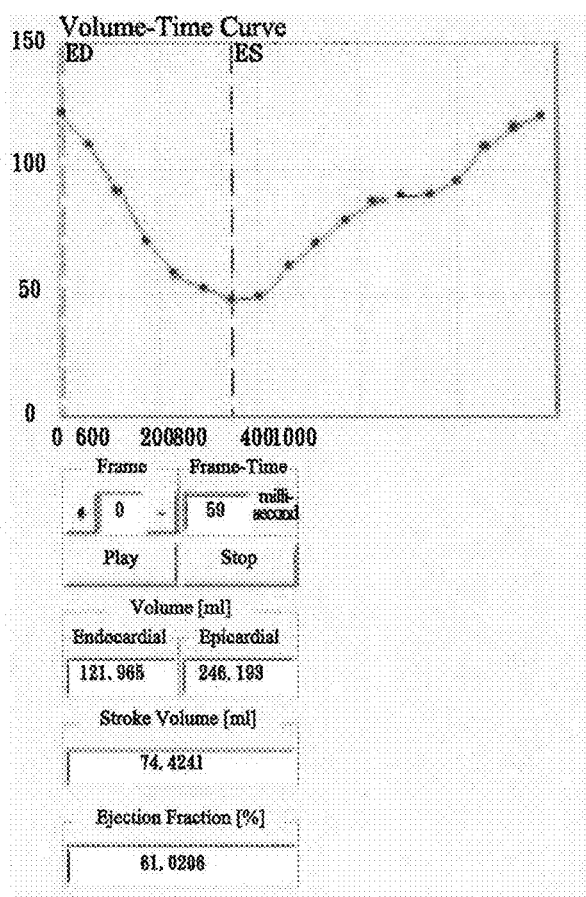
FIG. 6 schematically shows a volume evaluation parameter function according to an embodiment of the present invention.

Referring to FIG. 6, the volume parameter can be an end-diastolic volume (EDV), an end-systolic volume (ESV), a stroke volume (SV), or an ejection fraction (EF). To compute the volume parameter, the number of pixels in the area within the left ventricular contour in each cross-section is computed, and the numbers of pixels thus obtained are added up to produce the total number of volumetric pixels (i.e., voxels). Then, the total number of voxels is multiplied by a scaling factor, which is the actual size corresponding to each voxel, and a volume is obtained. After the volumes corresponding to an entire cycle of the left ventricle from diastole to systole are computed, a volume-time curve (VTC) is plotted. The lowest point (ES) of the volume-time curve represents the end-systolic volume, the highest point (ED) represents the end-diastolic volume, and the difference between the end-diastolic volume and the end-systolic volume is the stroke volume. The ejection fraction is the percentage obtained by dividing the stroke volume by the end-diastolic volume.

Figure 7:
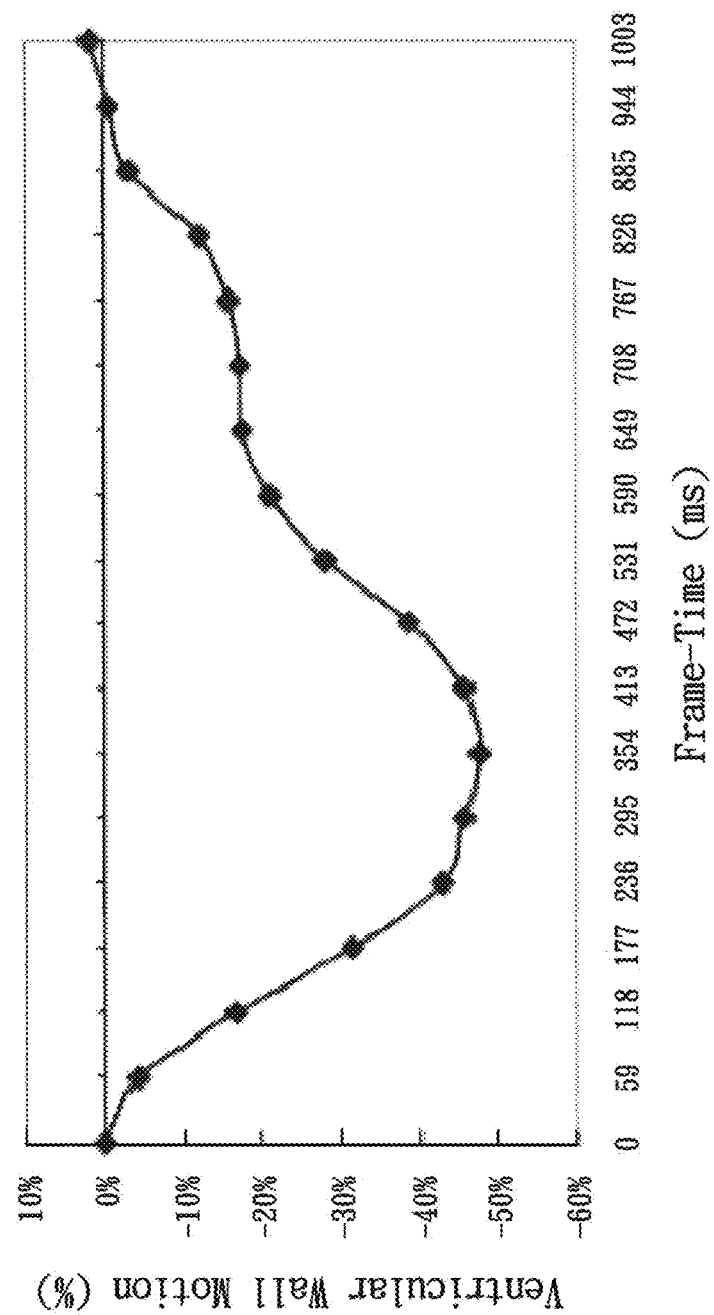
FIG. 7 shows a percent wall motion-time curve according to an embodiment of the present invention.

Referring to FIG. 7, the displacement parameter can be a ventricular wall motion parameter. As the heart pumps blood out of the ventricles by contraction of the ventricular wall, cardiac functions can be better understood by evaluating the contracting ability of each segment of the ventricular wall or the contracting ability of the ventricular wall as a whole. To compute the ventricular motion parameter, the difference between the endocardial contour in each cross-section of each segment of the ventricular wall (or of the entire ventricular wall) and the intersection point of the cross-sectional plane of the endocardial contour and the corresponding geometric center axis during a left ventricular wall moving period is computed and averaged, and the result is denoted by R. Also, the difference between the endocardial contour in each cross-section of each segment of the ventricular wall (or of the entire ventricular wall) and the intersection point of the cross-sectional plane of the endocardial contour and the corresponding geometric center axis at end diastole is computed and averaged, and the result is denoted by $R_{ed}$. The percent wall motion (% WM) is then calculated as $(R-R_{ed})/R_{ed} \times 100\%$. The ventricular wall can be divided in to six segments, namely a front segment, the anterior ventricular septum, the ventricular septum, a lower segment, a rear segment, and a lateral segment.

Figure 8:
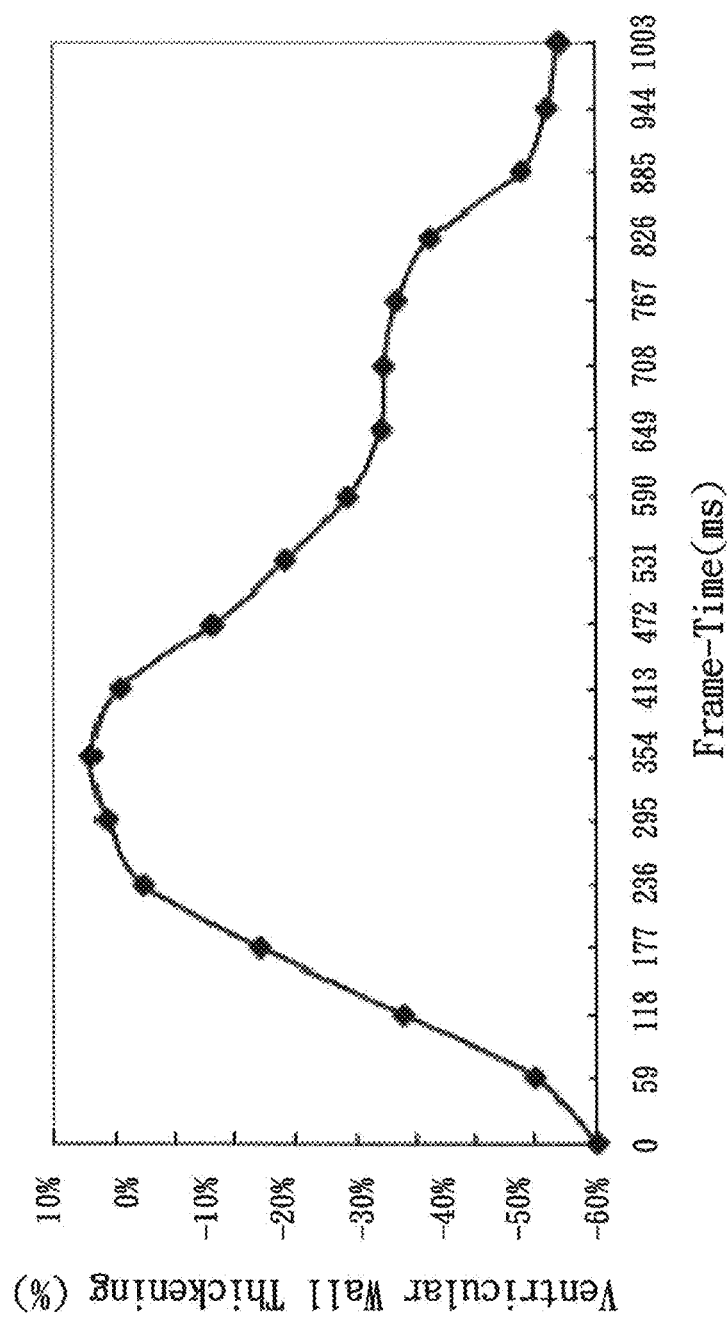
FIG. 8 shows a percent wall thickening-time curve according to an embodiment of the present invention.

Referring to FIG. 8, the deformation parameter can be a ventricular wall thickness parameter. As the contracting ability of the ventricular wall is related to the extent of myocardial contraction and relaxation, an understanding of how the ventricular wall thickness varies with cardiac muscle contraction and relaxation is helpful in the evaluation of cardiac functions. To compute the ventricular wall thickness parameter, the difference between each endocardial contour and the corresponding epicardial contour of each segment of the ventricular wall (or of the entire ventricular wall) during a left ventricular wall moving period is computed and averaged, and the result is denoted by T. In addition, the difference between each endocardial contour and the corresponding epicardial contour of each segment of the ventricular wall (or of the entire ventricular wall) at end diastole is computed and averaged, and the result is denoted by $T_{ed}$. The percent wall thickening (% WT) is then calculated as $(T-T_{ed})/T_{ed} \times 100\%$. The ventricular wall can be divided in to six segments, namely a front segment, the anterior ventricular septum, the ventricular septum, a lower segment, a rear segment, and a lateral segment.

The speed parameter can be a blood flow speed parameter for evaluating vascular functions. To compute the blood flow speed, a vascular volume is calculated by the foregoing method and then divided by the flow-out time.

Figure 9:
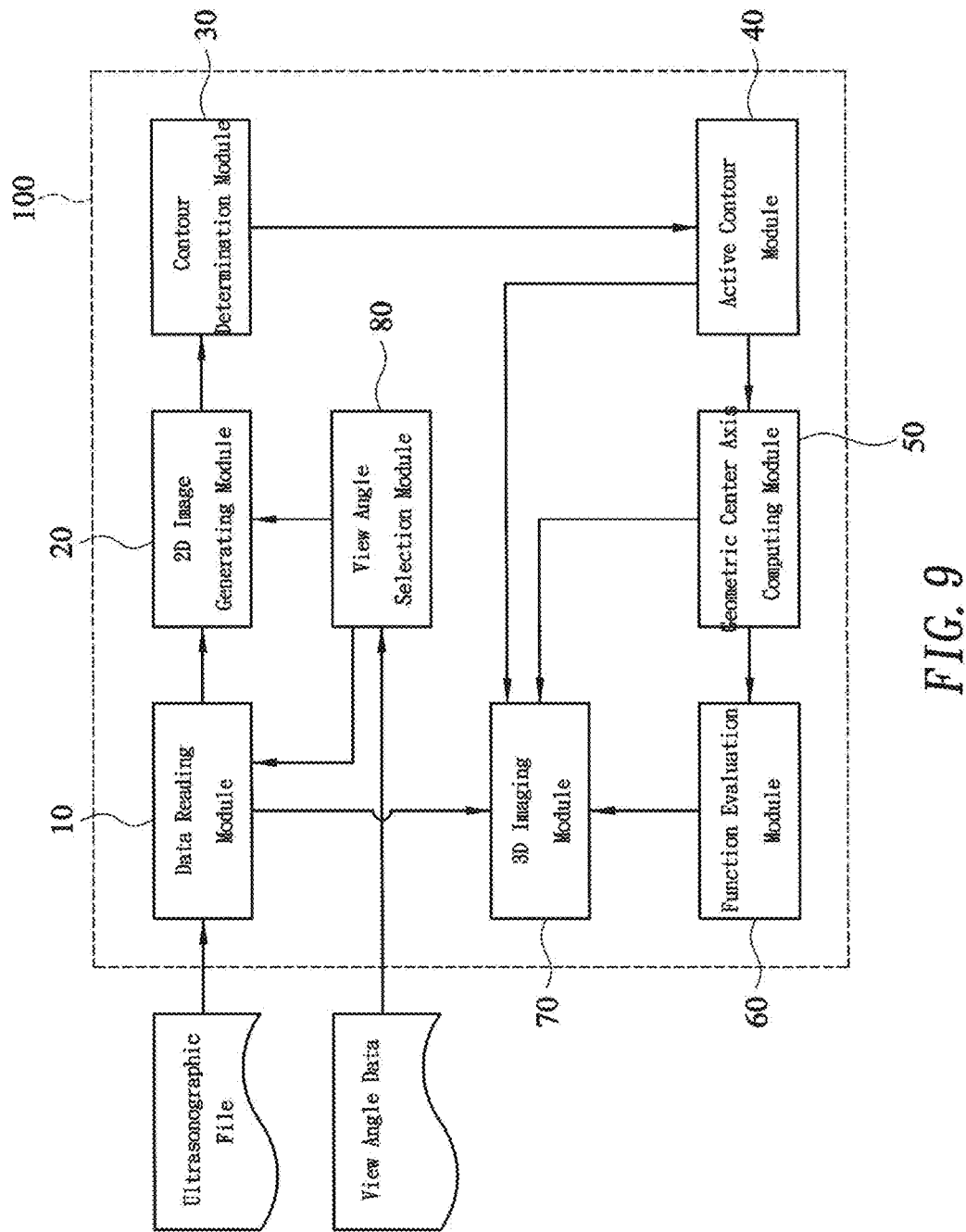
FIG. 9 is a block diagram showing the second aspect of the evaluation system according to the embodiment of FIG. 1.

Referring to FIG. 9, the evaluation system in this embodiment further includes a three-dimensional (3D) imaging module 70. The 3D imaging module 70 is configured for reading in real time the aforesaid 2D image files and the active contours 51 generated by the active contour module 40, computing with the files and the contours thus read, and then displaying a 3D image and an image showing the positions of the active contours 51. Using an advanced 3D image function of OpenGL API, the 3D imaging module 70 can enlarge, reduce, and rotate the 3D image and create such special effects as shedding light on and adding textures to the object in the 3D image.

Figure 10A:
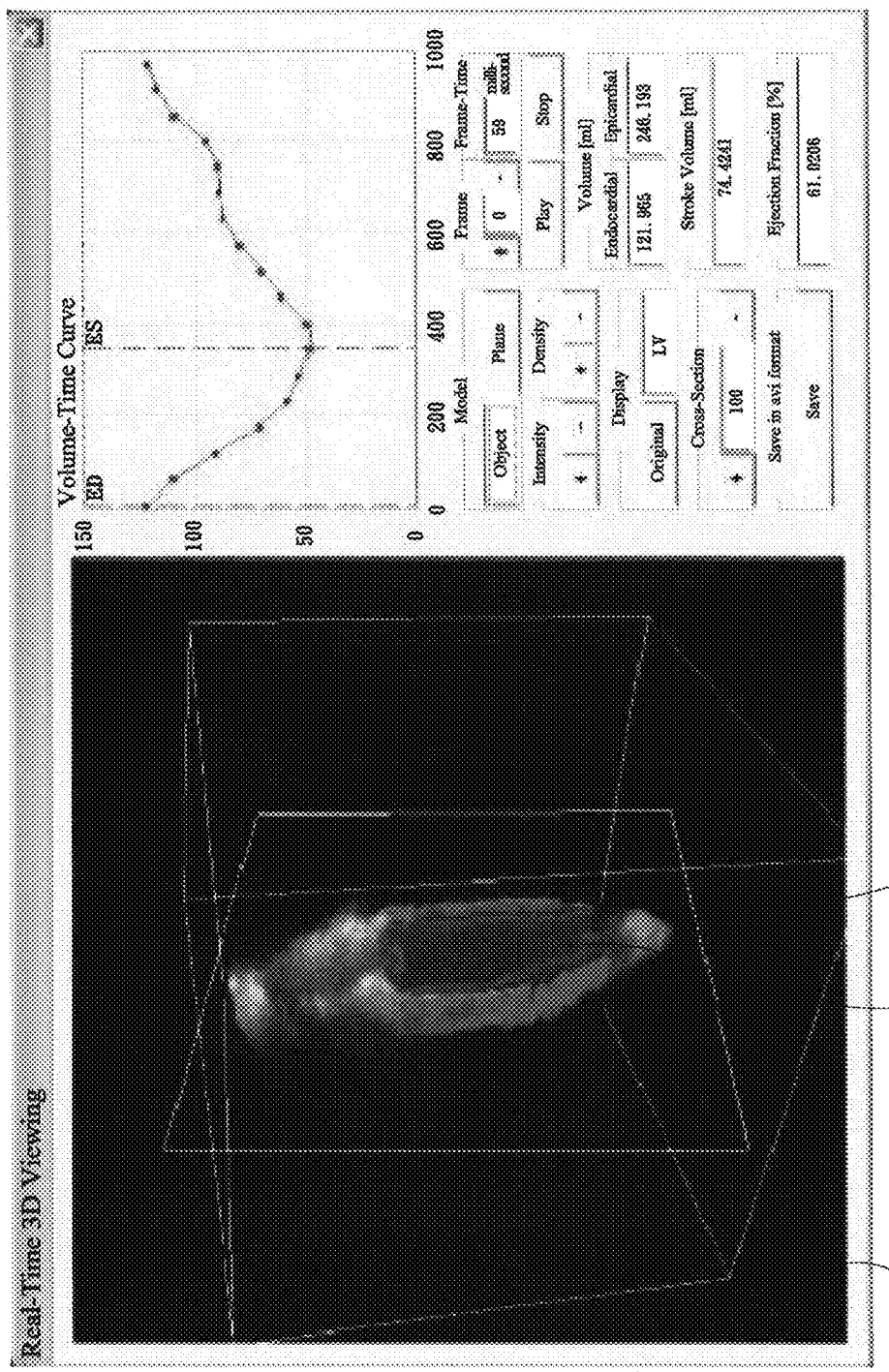
FIG. 10A schematically shows a real-time 3D viewing module interface according to an embodiment of the present invention.
Figure 10B:
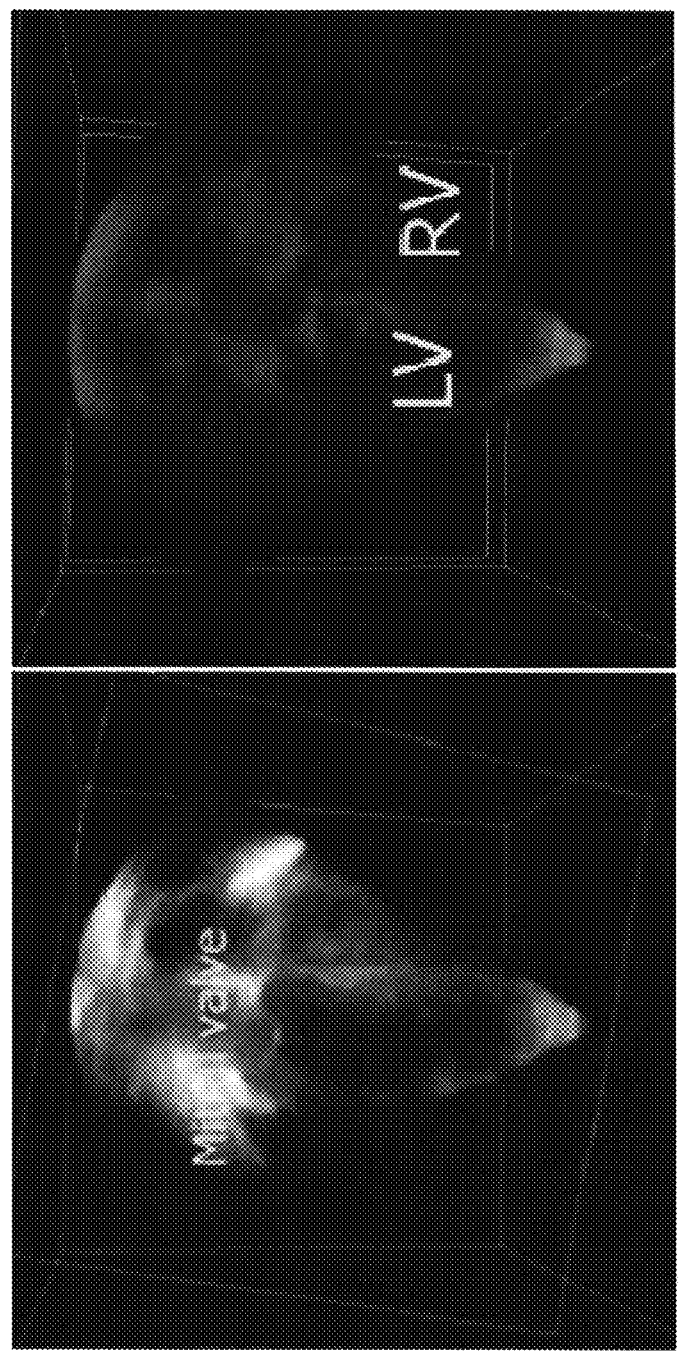
FIG. 10B shows an original heart model according to an embodiment of the present invention.
Figure 10C:
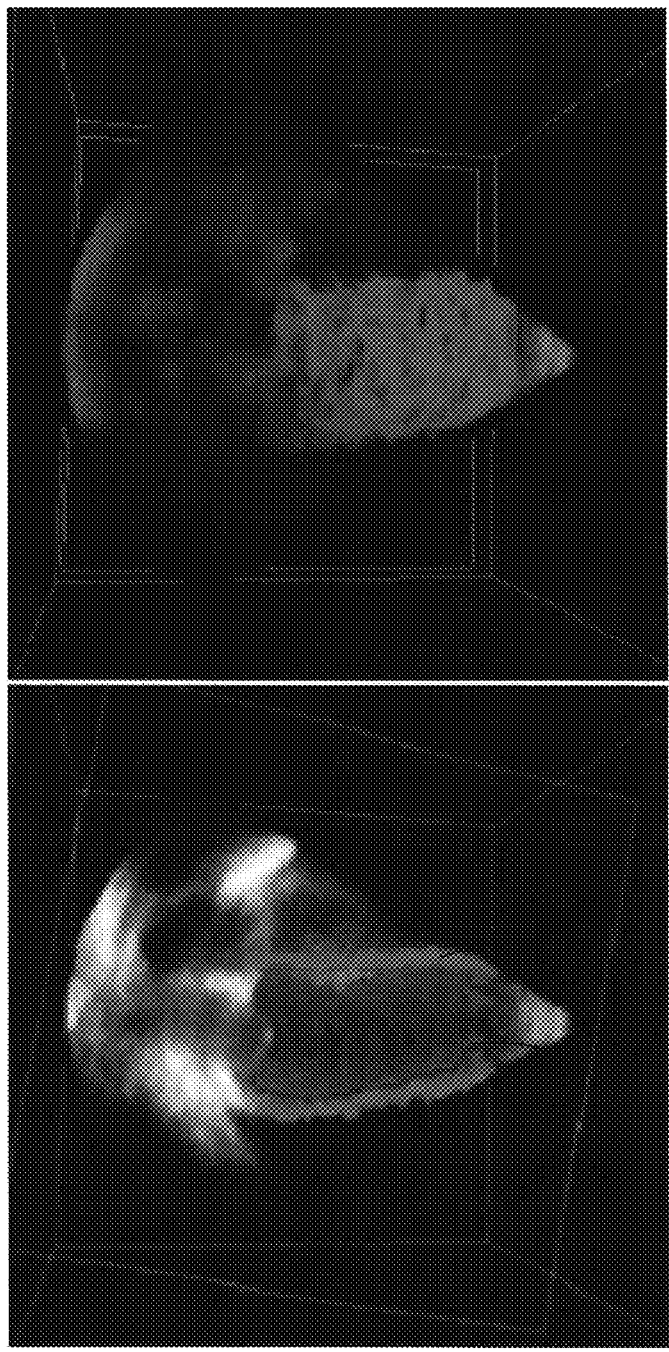
FIG. 10C shows a left ventricle module according to an embodiment of the present invention.

As shown in FIGS. 10A to 10C, when the Object button is selected, the viewing angle and viewing distance of the object in the display area 71 can be controlled by a dragging operation in conjunction with the left/right keys of a mouse. When the Plane button is selected, the position and angle of a cross-section in the display area 71 can be adjusted using the left/right keys of the mouse. Moreover, the 3D imaging module 70 allows selection of the range or portion to be displayed. By selecting the Original button, the original 3D heart model is displayed in its entirety; by selecting the LV button, the left ventricular endocardial contours 41 and the left ventricular epicardial contours 42 (highlighted by their respective active contours in red and green respectively) are displayed in addition to the original 3D heart model. Thus, the structural model and position of the entire left ventricle can be seen.

Figure 11A:
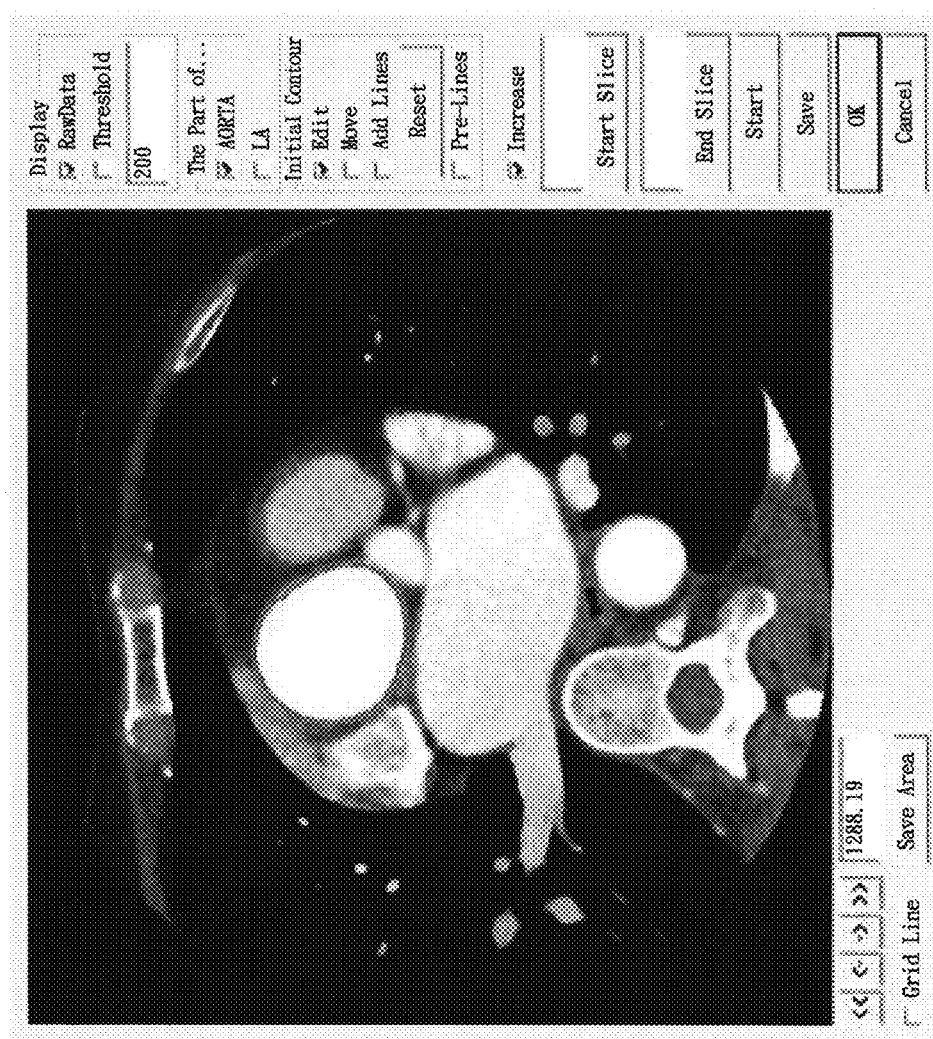
FIG. 11A is a perspective view of a 2D aortic cross-section image according to an embodiment of the present invention.
Figure 11C:
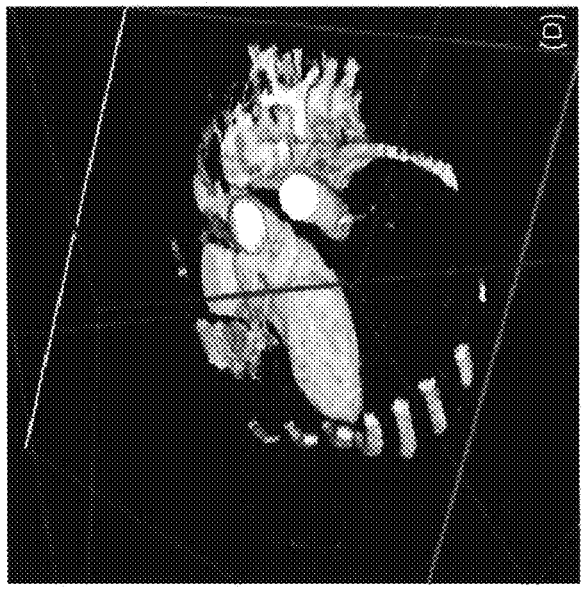
FIG. 11C is a perspective view of still another 2D aortic cross-section image according to an embodiment of the present invention.
Figure 11B:
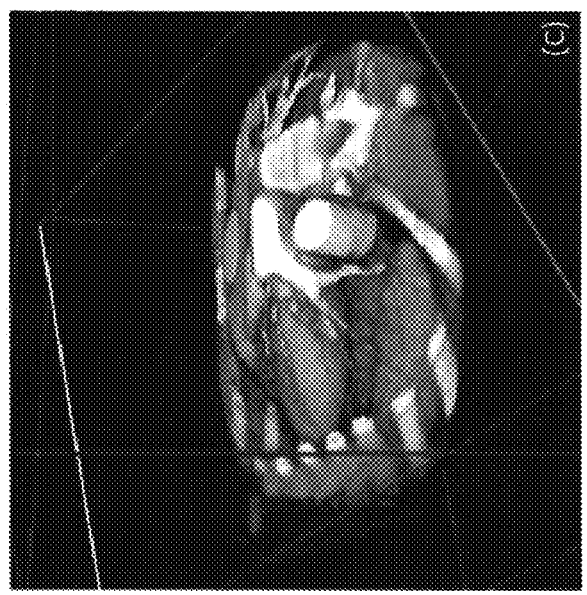
FIG. 11B is a perspective view of another 2D aortic cross-section image according to an embodiment of the present invention.

Please refer to FIGS. 11A to 11C, images of slices as shown in FIG. 11A construct a 3D image of an artery. Another view angle of the section of interest as shown in FIG. 11B can be obtained as in FIG. 11C to more clearly reveal the details needed for observations, both in still images and in motion images.

Figure 12C:
FIG. 12C is a perspective view of one of the cross-section images obtained from the 3D image of FIG. 12B.
Figure 12B:
FIG. 12B is a perspective view of a refined 3D image of a pulmonary according to an embodiment of the present invention.
Figure 12A:
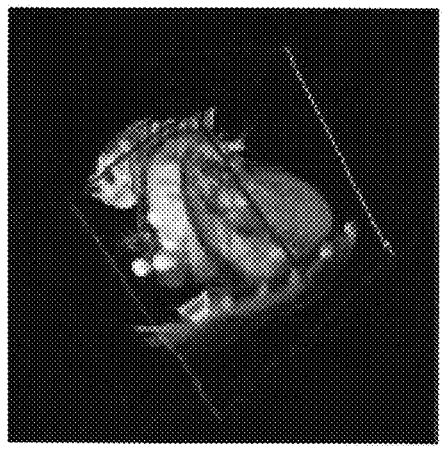
FIG. 12A is a perspective view of a reconstructed image of a pulmonary according to an embodiment of the present invention.
Figure 12E:
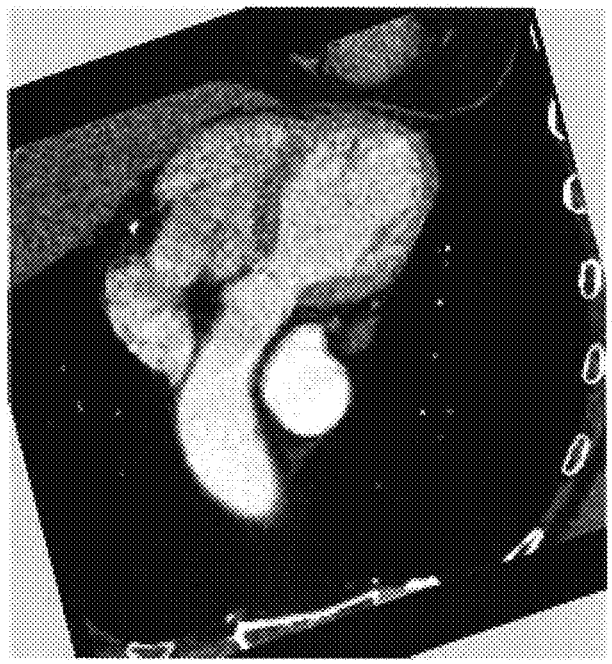
FIG. 12E is a perspective view of still another one of the cross-section images obtained from the 3D image of FIG. 12B.
Figure 12D:
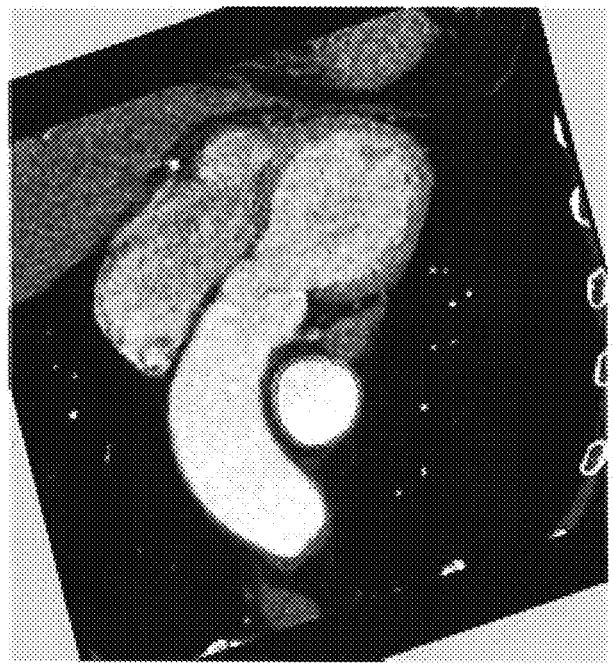
FIG. 12D is a perspective view of another one of the cross-section images obtained from the 3D image of FIG. 12B.
Figure 12F:
FIG. 12F is a perspective view of a reconstructed 3D image according to an embodiment of the present invention.

As shown in FIGS. 12A and 12B is a reconstructed image form slice images and a refined image of a pulmonary. FIG. 12C is a slice of the reconstructed and refined cross-section image taken from FIG. 12B, and FIGS. 12D to 12E are slices of cross-section images of also taken from FIG. 12B for better observations. While FIG. 12F is reconstructed from the slices of images based on the same view angle selected in FIG. 12C, wherein the red part defines a central region of observations.

Figure 13B:
FIG. 13B is a perspective view of a cross-section image of a left atrium and a left ventricular according to an embodiment of the present invention.
Figure 13A:
FIG. 13A is a perspective view of a cross-section image of a pulmonary according to an embodiment of the present invention.

As shown in FIGS. 13A and 13B are examples of slice images obtained on a same cross-section of the left atrium and left ventricular of a human heart. As can be seen, FIGS. 13A and 13B give detail images of the motion status of at least the pulmonary as pointed by the yellow arrow, and the intersection of the left atrium and the left ventricular as pointed by the blue arrow.

Figure 14A:
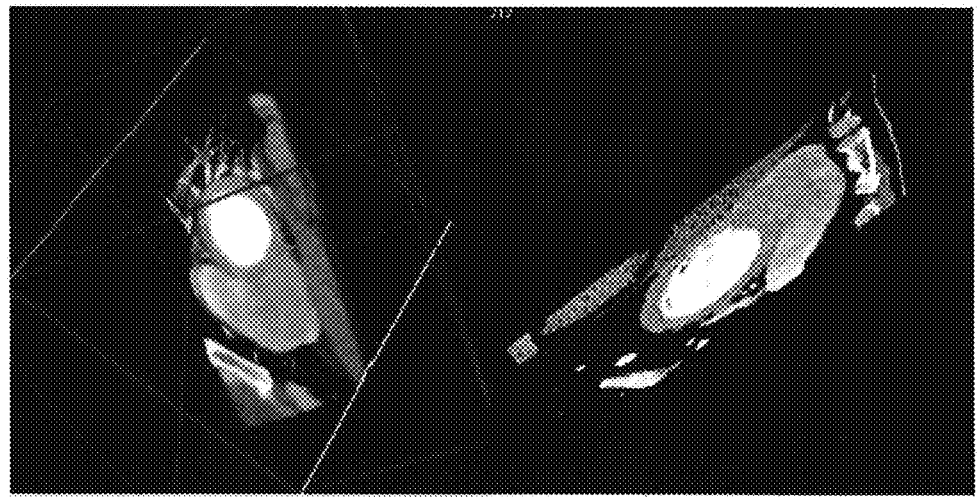
FIG. 14A is the comparison of 2 cross-section images from 2 different view angles of a left ventricular according to an embodiment of the present invention.
Figure 14B:
FIG. 14B is a cross-section image of a right ventricular according to an embodiment of the present invention.

As shown in FIG. 14A are 2 cross-section images from 2 different view angles of a left ventricular based on a reconstructed 3D image of the present invention. FIG. 14B is a cross-section image of a right ventricular based on another reconstructed 3D image of the present invention. As can be seen in FIG. 14B and defined by a blue indication line, the endocardial area is observed.

Figure 15:
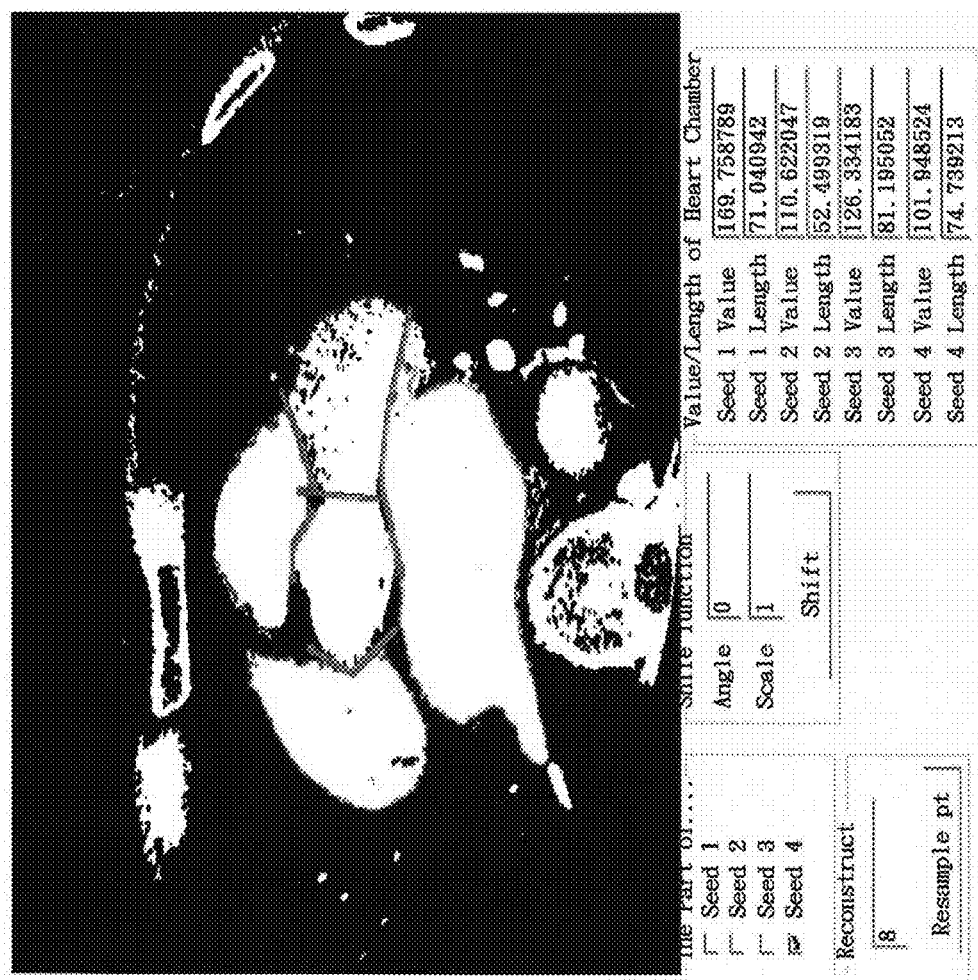
FIG. 15 is a cross-section image of a multiple-organ area according to an embodiment of the present invention.

As shown FIG. 15 is a cross-section of an image in an embodiment of an evaluation system 100, wherein multiple-organ observation is provided. The area denoted by a red line provides the area and length of the left ventricular, the area denoted by a red line provides the area and length of the left atrium, the area denoted by a blue line provides the area and length of the right ventricular, and the area denoted by a purple line provides the area and length of the right atrium.

Figure 16:
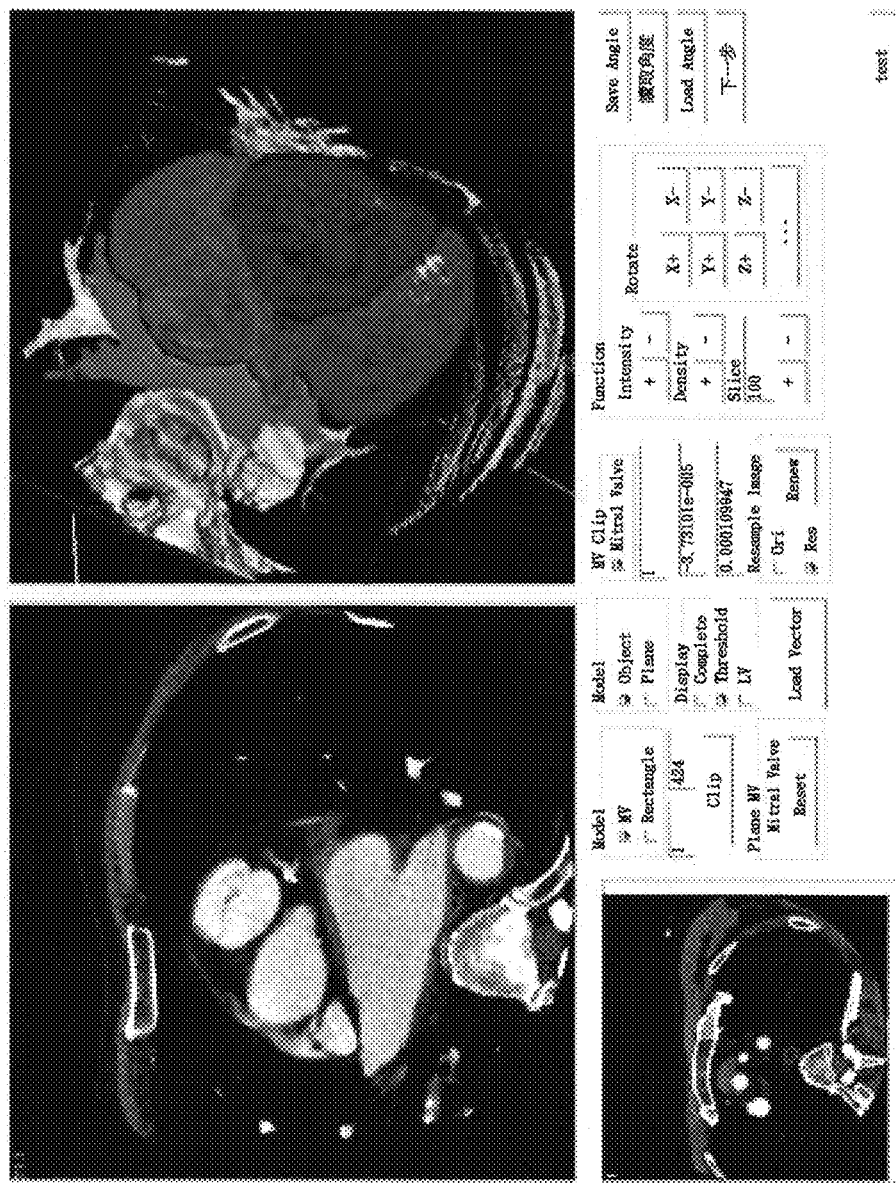
FIG. 16 is a perspective view of a display that provides both 2D cross-section image and 3D image of a chosen multiple-organ area according to an embodiment of the present invention.

As can also be seen in FIG. 16 is a display example of an embodiment of an evaluation system 100, both 2D cross-section image of a chosen view angle, and the 3D image of a chosen multiple-organ area can be displayed for ease of observation or analysis.

As such, simultaneous multiple-organ dynamic data acquisition and image analysis of cardiac ventricular, atriums and pulmonary can be made.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. An evaluation system for determination of cardiovascular function parameters, to be implemented in a computer hardware system, the evaluation system comprising:
   a data reading module for reading at least an graphic file, each said graphic file comprising a plurality of two-dimensional (2D) image files which are related to one another and are successively created at a plurality of time points in a time sequence;
   an image generating module for displaying the 2D image files as a plurality of 2D images and a 3D image constructed from the 2D images;
   a contour determination module for receiving point selection information generated by a user by selecting points in any said 2D image corresponding to an initial said time point, and for determining an initial contour in each said 2D image corresponding to the initial time point according to the point selection information;
   an active contour module for reading the initial contours and determining an active contour in each said 2D image;
   a geometric center axis computing module for reading the active contours and computing a geometric center axis corresponding to each said time point;
   a view angle selection module, which receives a view angle data, rotates the 3D image according to the view angle data and modify the 2D image files read by the data reading module accordingly to generate plural cross-section images of the 3D image relative to the view angle data received; and
   a function evaluation module for successively computing a difference between the active contours corresponding to each said time point in the time sequence and a corresponding said geometric center axis, and for generating an evaluation parameter accordingly.

2. The evaluation system of claim 1, wherein each said graphic file is a Digital Imaging and Communications in Medicine (DICOM) file, a CT (computer tomography) data file, a MRI data file or an ultrasonographic data file.

3. The evaluation system of claim 1, wherein each said initial contour comprises an initial endocardial contour and an initial epicardial contour.

4. The evaluation system of claim 1, wherein each said active contour comprises an active endocardial contour and an active epicardial contour.

5. The evaluation system of claim 1, wherein the geometric center axes are determined by a curvature method.

6. The evaluation system of claim 1, wherein the geometric center axes are a mechanical center axis of a heart.

7. The evaluation system of claim 1, further comprising a three-dimensional (3D) imaging module for reading and computing with the 2D image files and the active contours and displaying a 3D image and an image showing positions of the active contours.

8. The evaluation system of claim 1, wherein the evaluation parameter is one of a volume parameter, a displacement parameter, a deformation parameter, and a speed parameter.

9. The evaluation system of claim 8, wherein the volume parameter is one of an end-diastolic volume, an end-systolic volume, a stroke volume, and an ejection fraction.

10. The evaluation system of claim 8, wherein the displacement parameter is a ventricular wall motion parameter.

11. The evaluation system of claim 8, wherein the deformation parameter is a ventricular wall thickness parameter.

* * * * *